(12) United States Patent
Liphardt et al.

(10) Patent No.: US 7,136,162 B1
(45) Date of Patent: Nov. 14, 2006

(54) ALIGNMENT OF ELLIPSOMETER BEAM TO SAMPLE SURFACE

(75) Inventors: Martin M. Liphardt, Lincoln, NE (US); Craig M. Herzinger, Lincoln, NE (US); Brian D. Guenther, Lincoln, NE (US); Steven E. Green, Lincoln, NE (US); Galen L. Pfeiffer, Lincoln, NE (US); Ping He, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 359 days.

(21) Appl. No.: 10/684,088

(22) Filed: Oct. 12, 2003

Related U.S. Application Data

(60) Provisional application No. 60/459,690, filed on Apr. 3, 2003, provisional application No. 60/418,266, filed on Oct. 15, 2002.

(51) Int. Cl.
*G01J 4/00* (2006.01)

(52) U.S. Cl. .................................................... 356/369

(58) Field of Classification Search ................ 356/369, 356/636, 634
See application file for complete search history.

(56) References Cited

U.S. PATENT DOCUMENTS

| | | | |
|---|---|---|---|
| 4,373,817 A | 2/1983 | Coates | 356/384 |
| 4,742,376 A * | 5/1988 | Phillips | 355/77 |
| 4,957,367 A * | 9/1990 | Dulman | 356/512 |
| 5,042,951 A * | 8/1991 | Gold et al. | 356/369 |
| 5,045,704 A | 9/1991 | Coates | 250/372 |
| RE34,783 E | 11/1994 | Coates | 250/372 |
| 5,486,701 A | 1/1996 | Norton et al. | 250/372 |
| 5,596,411 A | 1/1997 | Fanton et al. | 356/369 |
| 5,608,526 A | 3/1997 | Piwonka-Corle et al. | 356/364 |
| 5,793,480 A * | 8/1998 | Lacey et al. | 356/73 |
| 5,889,593 A | 3/1999 | Bareket | 356/445 |
| 5,900,939 A | 5/1999 | Aspnes et al. | 356/369 |
| 5,910,842 A * | 6/1999 | Piwonka-Corle et al. | 356/369 |
| 6,259,174 B1 * | 7/2001 | Ono | 310/13 |
| 6,297,880 B1 * | 10/2001 | Rosencwaig et al. | 356/369 |
| 6,590,656 B1 * | 7/2003 | Xu et al. | 356/369 |
| 6,600,560 B1 | 7/2003 | Mikkelsen et al. | 356/369 |
| 6,650,419 B1 * | 11/2003 | Hill | 356/500 |
| 6,700,665 B1 * | 3/2004 | Hill | 356/500 |
| 6,982,792 B1 * | 1/2006 | Woollam et al. | 356/369 |

* cited by examiner

*Primary Examiner*—Gregory J. Toatley, Jr.
*Assistant Examiner*—Isiaka O. Akanbi
(74) *Attorney, Agent, or Firm*—James D. Welch

(57) ABSTRACT

Disclosed is a system and method of aligning, preferably by an automated procedure, a beam of electromagnetic radiation provided by a source thereof so that it approaches a sample at a specific location upon its surface, at a known angle, then reflects therefrom and enters a data detector.

18 Claims, 3 Drawing Sheets

ALIGNMENT OF ELLIPSOMETER BEAM TO SAMPLE SURFACE

This Application Claims Benefit of Provisional Applications Nos. 60/418,266 Filed Oct. 15, 2002 and 60/459,690 Filed Apr. 3, 2003.

TECHNICAL AREA

The disclosed invention relates to ellipsometer, polarimeter, reflectometer, spectrophotometer and the like systems, and more particularly is a system and method of aligning, preferably by an automated procedure, a beam of electromagnetic radiation provided by a source thereof so that it reflects from said substantially flat surface at a known angle and plane of incidence, and enters a data detector.

BACKGROUND

It is known to provide a source of electromagnetic radiation and cause it to reflect perpendicularly from a surface of a sample so that the orientation of the source of the electromagnetic beam is known, then to rotate/tilt the sample to set it such that said electromagnetic beam approaches it along an oblique angle, and then to move the sample in a direction perpendicular to its surface so that a reflected electromagnetic beam enters a present data detector. Said technique is utilized in the J.A. Woollam CO. VUV-VASE System, for instance.

It is also known to focus a beam of electromagnetic radiation which approaches a surface of a sample onto a very small spot and reflects therefrom, and without tending to any sample rotation/tilting move the sample along a substantial perpendicular to said sample surface until a reflected beam optimally enters a present detector. Where a focused beam is utilized the spot size is sufficiently small that a slight tilt of the sample has little effect on the trajectory of the reflected beam. This technique is utilized in systems produced by Nanometrics Inc.

The above recited approaches to aligning a sample with respect to an electromagnetic beam, it should be appreciated, utilize only one beam of electromagnetic radiation.

A Co-Pending Application discloses a system for controlling the angle of incidence and angle of azimuth at which a beam of electromagnetic radiation obliquely impinges on a monitored location of a surface of a sample which comprises a sample supporting stage which can be translated in "X", "Y" and "Z" directions as well as rotated about "X", "Y" and optionally "Z" axes. (Note that this is to be interpreted to include rotating and translating the ellipsometer such that relative positioning of the sample and ellipsometer is achieved). Said system is primarily for application with samples with irregular surfaces, or small samples. Vertically, as viewed in side elevation, above said stage there is a first beam splitter means, a lens and a first camera means for providing a view of a portion of the surface of said sample, said first beam splitter means having optionally positioned below a lower surface thereof, light emitting means for providing light to the surface of said sample. Laterally with respect to said first beam splitter means there being a reflection means, and vertically above said reflection means there being a second beam splitter. Vertically above said second beam splitter there is a second camera means and laterally with respect to said second beam splitter, there is sequentially a lens and an essentially point source of electromagnetic radiation. Said first and second camera means each have associated therewith display means. Said system further comprises an ellipsometer polarization state generator to cause, and a polarization stage detector to monitor, a beam of electromagnetic radiation which in use impinges on said monitored location on said surface of said sample at an oblique angle thereto. In use said first camera means and its associated display means provide a view of at least a portion of the surface of a sample utilizing light provided by said light emitting means for providing light to the surface of said sample positioned on said lower surface of said first beam splitter, and said essentially point source of a source of electromagnetic radiation provides electromagnetic radiation to the surface of said sample via said second beam splitter, said reflective means and said first beam splitter. Said sample supporting stage is caused to be translated in any of said "X", "Y" and "Z" directions as well as rotated about said "X", "Y" and optionally "Z" axes which are necessary to cause an interrogating beam of electromagnetic radiation provided by said essentially point source, (eg. a fiber optic), of a source of electromagnetic radiation to reflect from the surface of said sample, proceed back through said first beam splitter means, reflect from said reflective means, pass through said second beam splitter means, enter said second camera means and cause an image on the display means associated therewith which indicates, (eg. via an electronically generated cross-hair), that the monitored location on the sample surface is oriented so as to face substantially vertically. The purpose is to align said sample surface to assure that said beam of electromagnetic radiation provided to said monitored location on the surface of said sample at an oblique angle approaches said surface at a known intended angle of incidence thereto, rather than at an angle of incidence which is modified by surface irregularities or non-flat samples, (eg. wedge shaped). A problem can develop in that an interrogation beam spot can appear in the image of the first camera means display as part of the interrogation beam and proceed through said first beam splitter thereinto. As a solution to this problem, said system can further provide that a polarizer means be placed into the path of said beam of electromagnetic radiation provided by said essentially point source of a source of electromagnetic radiation, and in which said first beam splitter is sensitive to polarization state. The polarizer means is preferably adjustable to enable changing the direction of imposed polarization. This can be beneficial where, for instance, the sample has an effect on the reflected interrogation beam polarization state, and where it is determined desirable to allow some of said interrogation beam to reach the first camera means, (eg. where it is found to aid with sample surface alignment).

It is noted as an introduction to the following method that when the sample surface is oriented to face substantially vertically at said monitored location, limited range "X" and/or "Y" translation has essentially no effect on said image on the display means associated with said second camera means, thereby indicating that the monitored location on said sample surface is oriented so as to face substantially vertically over said limited range of "X" and "Y" translation. (It is noted that a standard ellipsometer alignment detector means is used to achieve this step). Of course gross "X" and/or "Y" translation does have an effect which is representative of surface irregularities.

It is noted that a sample with surface irregularities was used as an example in the foregoing, but the sample can also be very small, (eg. millimeter dimensions), which presents similar alignment difficulties.

The method of calibration involving orientating a monitored location on a sample, said sample being characterized by:

it has surface irregularities, or it is small in dimension;

comprises the steps of:

a) providing a stage for supporting a sample, said stage having means for effecting translation in any of said "X", "Y" and "Z" directions as well as rotation about said "X", "Y" and optionally "Z" axes;

b) placing a sample characterized by a selection from the group consisting of:

it has surface irregularities, it is small in dimension;

onto surface onto said stage;

c) causing an interrogating beam of electromagnetic radiation to impinge on said monitored location on said sample;

d) monitoring the effect of "X" and "Y" direction translation on the locus of reflected beam electromagnetic radiation from the surface said sample and if either said translation causes significant change therein practicing step e, and if neither said translation causes significant change therein terminating the practice of said method;

e) adjusting rotation of said stage about at least one of the "X" and "Y" directions and again monitoring practicing step d.

Said method of calibration can further comprises at least one "Z" direction translation to better enable monitoring the effect of "X" and "Y" direction translation on the locus of reflected beam electromagnetic radiation from the surface of said sample.

While a specific Search was not conducted, known patents are disclosed to aid the Examination:

patent to Coates U.S. Pat. No. 4,373,817;

patent to Coates U.S. Pat. No. 5,045,704;

RE. 34,783 to Coates;

patent to Mikkelsen et al., U.S. Pat. No. 6,600,560;

patent to Fanton et al., U.S. Pat. No. 5,596,411;

patent to Piwonka-Corle et al., U.S. Pat. No. 5,910,842;

patent to Piwonka-Corle et al., U.S. Pat. No. 5,608,526;

patent to Bareket, U.S. Pat. No. 5,889,593;

patent to Norton et al., U.S. Pat. No. 5,486,701;

patent to Aspnes et al., U.S. Pat. No. 5,900,939;

PCT Application Publication WO 99/45340;

Published Application of Stehle et al., No. US2002/0024668 A1;

While the known prior art and a previously disclosed system and method provide means for aligning a sample, there remains need for a simple system and method for aligning samples in ellipsometer, polarimeter, reflectometer, spectrophotometer and the like systems, particularly where applied to large area samples.

DISCLOSURE OF THE INVENTION

The presently disclosed invention is focused on aligning a stage/sample, (eg. a large area flat panel for instance), with respect to a beam of electromagnetic radiation utilizing two beams of electromagnetic radiation. The presently disclosed system provides a Multi-element, (eg. at least Two elements and typically a Quad-Detector), sensor system which allows for entering a first beam of electromagnetic radiation through a centrally located opening therein and causing said beam to approach and reflect from the surface of the sample. The method of the presently disclosed invention then provides that the stage/sample be then tilted until the first electromagnetic beam reflects directly back therefrom and therefore ideally does not enter any of the Multiple Detectors which surround the centrally located opening. This determines the orientation of the surface of the with respect to said first electromagnetic beam. The presently disclosed invention system further provides a source of a second beam of electromagnetic radiation, (it being oriented with respect to the first beam of electromagnetic radiation in a known way), from which a second beam of electromagnetic radiation is caused to approach the surface of the sample at an oblique angle, reflect therefrom and proceed generally toward a provided detector. The method of the presently disclosed invention then provides for moving the stage/sample along a perpendicular to the surface of the sample until the data detector is found to receive an electromagnetic beam of a maximum intensity.

In the following a system comprising a four element Quad-Detector will be used as an non-limiting example, however, it should be appreciated that the Detector can comprise any functional number of elements.

A preferred presently disclosed system for aligning a sample can be described as comprising:

a pivot mounted stage/sample; and a means for imparting translation motion to said pivot mounted stage/sample substantially along a perpendicular to a surface thereof;

a first source of a first beam of electromagnetic radiation in functional combination with a Quad Detector comprised of at least four detector element surrounding a hole therethrough; and a second source of a second beam of electromagnetic radiation; and data detector.

The first source of a first beam of electromagnetic radiation is oriented so as to provide a first beam of electromagnetic radiation through a hole in said Quad Detector, wherein said Quad Detector is comprised of at least four detector elements surrounding said hole therethrough. The pivot mounted stage/sample is positioned to receive said first beam of electromagnetic radiation substantially along a normal to a surface of said pivot mounted stage/sample via said hole in said quad detector. Said second source of electromagnetic radiation is positioned to provide a beam of electromagnetic radiation and direct it to the surface of said sample at an oblique angle thereto, such that said second beam of electromagnetic radiation reflects from said surface of said pivot mounted stage/sample. The first and second electromagnetic beams being oriented with respect to one another at a known angle. Said pivot mounted stage/sample is mounted to said means for imparting translation motion such that said pivot mounted stage/sample can be caused to move substantially along a perpendicular to the surface thereof, such that the reflected second beam of electromagnetic radiation enters said data detector.

A method of aligning a sample comprises the steps of:

a) system for aligning a sample as described;

b) causing a first beam of electromagnetic radiation from said first source of a first beam of electromagnetic to pass through said hole in the Quad Detector such that said first beam of electromagnetic radiation reflects from the surface of said pivot mounted stage/sample;

c) pivoting said sample about said stage/sample pivot mounting until signals from all of the Quad Detector detector elements are substantially minimized or equalized, indicating that said first beam of electromagnetic radiation approaches said surface of said sample substantially along a normal thereto;

d) causing said second source of electromagnetic radiation to provide a beam of electromagnetic radiation and direct it to the surface of said sample at an oblique angle thereto, such that said second beam of electromagnetic radiation reflects from said surface of said pivot mounted stage/sample;

e) optionally causing said pivot mounted stage/sample to undergo translation motion substantially perpendicular to the surface of said sample via said means for imparting translation motion to said pivot mounted stage/sample;

such that the reflected second beam of electromagnetic radiation is directed to enter said data detector. Steps c. and e. are preferably automated.

The method can be repeated at another location on the sample, especially where the sample is relatively large, (eg. 450 mm square).

A modified system for aligning a sample comprising:

a pivot mounted stage/sample;

a means for imparting translation motion to said pivot mounted stage/sample substantially along a perpendicular to a surface thereof;

a first source of a first beam of electromagnetic radiation in functional combination with a beam splitter and a multi-element alignment detector comprised of at least two detector elements; and a second source of a second beam of electromagnetic radiation; and a data detector.

Said first source of a first beam of electromagnetic radiation is oriented so as to transmit a first beam of electromagnetic radiation through said beam splitter and said pivot mounted stage/sample is positioned to receive said first beam of electromagnetic radiation substantially along a normal to a surface of said pivot mounted stage/sample via said beam splitter. Said multi-element alignment detector is positioned to receive electromagnetic radiation reflected from said surface of said sample which is reflected from said beam splitter. Said second source of electromagnetic radiation is positioned to provide a beam of electromagnetic radiation and direct it to the surface of said sample at an oblique angle thereto, such that said second beam of electromagnetic radiation reflects from said surface of said pivot mounted stage/sample, and said first and second electromagnetic beams being oriented with respect to one another at a known angle. Said pivot mounted stage/sample is mounted to said means for imparting translation motion such that said pivot mounted stage/sample can be caused to move substantially along a perpendicular to the surface thereof, such that the reflected second beam of electromagnetic radiation enters said data detector.

A method of aligning a sample comprising the steps of:

a) providing a system for aligning a sample as just described:

b) causing a first beam of electromagnetic radiation from said first source of a first beam of electromagnetic to pass through said beam splitter such that said first beam of electromagnetic radiation reflects from the surface of said pivot mounted stage/sample, then reflects from said beam splitter and enters said multi-element alignment detector;

c) pivoting said sample about said stage/sample pivot mounting until signals from all of the multi-element alignment detector detector elements are substantially minimized or equalized, indicating that said first beam of electromagnetic radiation approaches said surface of said sample substantially along a normal thereto;

d) causing said second source of electromagnetic radiation to provide a beam of electromagnetic radiation and direct it to the surface of said sample at an oblique angle thereto, such that said second beam of electromagnetic radiation reflects from said surface of said pivot mounted stage/sample;

e) optionally causing said pivot mounted stage/sample to undergo translation motion substantially perpendicular to the surface of said sample via said means for imparting translation motion to said pivot mounted stage/sample; such that the reflected second beam of electromagnetic radiation is directed to enter said data detector.

As before, steps c. and e. can be automated, and said method can be repeated at another location on the sample. Automation can be achieved by feeding the signals from alignment detector detector elements into a processor which detects differences therein, and by detecting output from the Data Detector, then in response adjusting the tilt and/or vertical positioning of the sample to minimize differences in signal outputs from the detector elements in the Alignment Detector, and to establish or increase signal from the Data Detector.

Further, while the first and beams of electromagnetic radiation from the first and second sources of electromagnetic radiation are typically caused to both impinge on the sample surface at substantially the same spot, it is to be appreciated that it is within the scope of the disclosed invention to cause said first and second beams to impinge at different locations on a sample surface.

The disclosed invention will be better understood by reference to the Detailed description Section in combination with the Drawings.

DETAILED DESCRIPTION

Figure 1A:
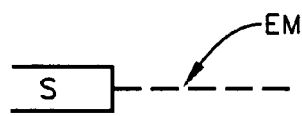
FIG. 1a shows a Source (S) of a beam of electromagnetic radiation (EM).
Figure 1B:
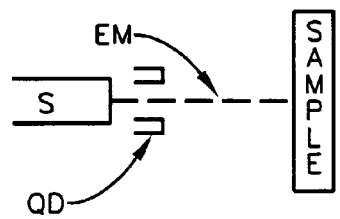
FIG. 1b shows a Source (S) of a beam of electromagnetic radiation (EM) reflecting directly back from a Sample. A Quad Detector is shown which is used to align the sample.
Figure 1C:
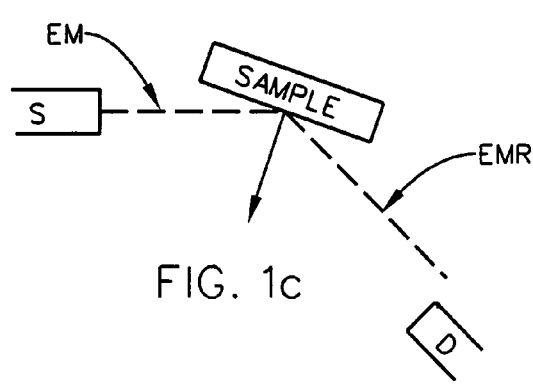
FIG. 1c shows the Sample of FIG. 1b rotated so that the beam of electromagnetic radiation (EM) approaches its surface along an intended oblique angle.
Figure 1D:
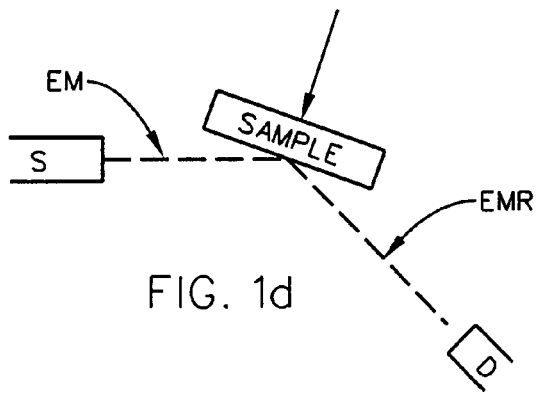
FIG. 1d shows the Sample in FIG. 1c has been moved along a perpendicular to the surface thereof, to the end that the reflected electromagnetic beam (EMR) entered the data detector (D).

Turning now to the Drawings, it is noted that FIGS. 1a–2b demonstrate Prior Art single electromagnetic beam source systems and methods for aligning a sample. FIG. 1a a Single Source (S) of a beam of electromagnetic radiation (EM). FIG. 1b shows said beam of electromagnetic radiation (EM) reflecting directly back from a surface of a Sample. A Quad Detector (QD) is shown which is used to align the sample. When the electromagnetic beam reflects directly back, the Quad Detector detector elements do not detect any input. FIG. 1c shows the Sample of FIG. 1b rotated so that the beam of electromagnetic radiation (EM) approaches its surface along an intended and known oblique angle. FIG. 1d shows the Sample in FIG. 1c has been moved along a perpendicular to the surface thereof, to the end that the reflected electromagnetic beam (EMR) enters the data detector (D).

Figure 2A:
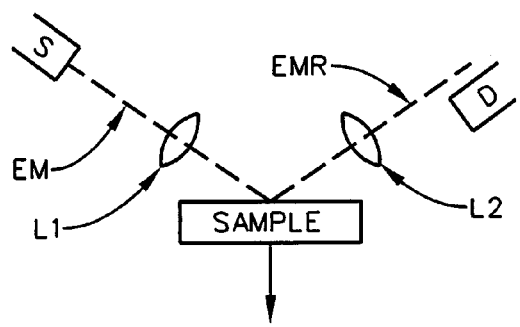
FIG. 2a shows a Source (S) of a beam of electromagnetic radiation (EM) approaching a surface of a Sample along an intended oblique angle, with a beam of electromagnetic radiation (EMR) shown reflecting therefrom. Also shown is a Detector (D).
Figure 2B:
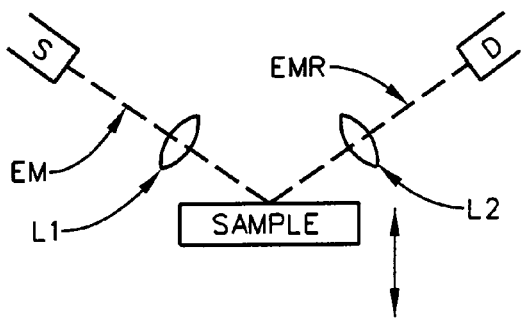
FIG. 2b shows the Sample in FIG. 2a has been moved along a perpendicular to its surface to cause the reflected beam of electromagnetic radiation (EMR) to enter the Detector (D).

FIG. 2a shows a Single Source (S) of a beam of electromagnetic radiation (EM) approaching a surface of a Sample along an intended oblique angle, with a beam of electromagnetic radiation (EMR) shown reflecting therefrom. Also shown is a Detector (D). FIG. 2b shows the Sample in FIG. 2a has been moved along a perpendicular to its surface to cause the reflected beam of electromagnetic radiation (EMR) to enter the Detector (D). This system and method of alignment can be used where the beam is highly focused onto a small spot on a sample by use of achromatic lenses (L1) and (L2).

Figure 3A:
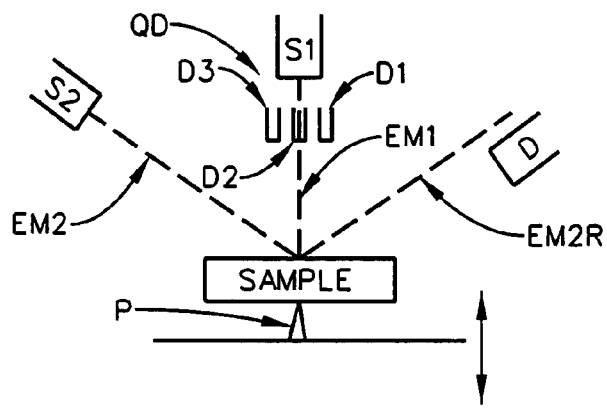
FIG. 3a shows a present invention system comprised of a First Source (S1) of a First beam of electromagnetic radiation (EM1), a Quad Detector (QD) for which are shown detector element D1, D2 and D3, a Second Source (S2) of a Second beam of electromagnetic radiation (EM2), a Pivot (P) mounted Sample, and a Detector (D).
Figure 3B:
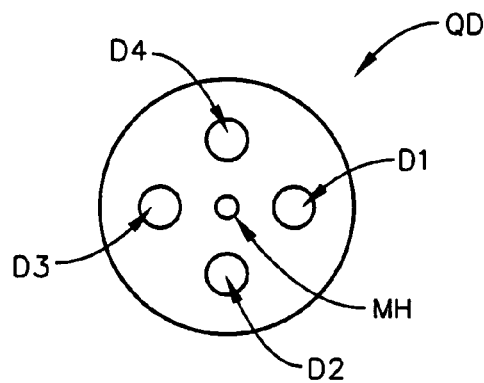
FIG. 3b shows a top view of a Quad Detector.

FIG. 3a shows a present invention system comprised of a First Source (S1) of a First beam of electromagnetic radiation (EM1), an Multi-element (eg. Quad) Detector (QD), a Second Source (S2) of a Second beam of electromagnetic radiation (EM2), a Pivot (P) mounted Sample, and a Detector (D). In use the Multi-element Detector (QD) is used to aid orienting the Sample via pivoting about Pivot mount (P) so that electromagnetic beam (EM1) approaches and reflects at 90 degrees to the Surface of the Sample. Note however that the electromagnetic beam (EM2R) which, reflects from the Sample at an oblique angle does not enter the Detector (D). FIG. 3b shows the Pivot mounted Sample moved along a perpendicular to its surface so that a Reflected beam of electromagnetic radiation (EM2) enters the Detector (D). FIGS. 3a and 3b then demonstrate a new presently disclosed two beam approach to sample alignment which is useful where the sample is a panel with dimensions on the order of 450 mm square.

Figure 3C:
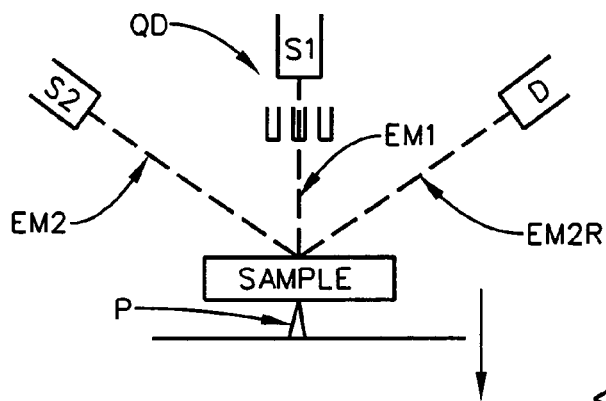
FIG. 3c shows the Pivot mounted Sample moved along a perpendicular to its surface so that a Reflected beam of electromagnetic radiation (EM2) enters the Detector (D).

FIG. 3c shows the Pivot mounted Sample moved in translation along a perpendicular to its surface so that a Reflected beam of electromagnetic radiation (EM2) enters the Detector (D).

Figure 3D:
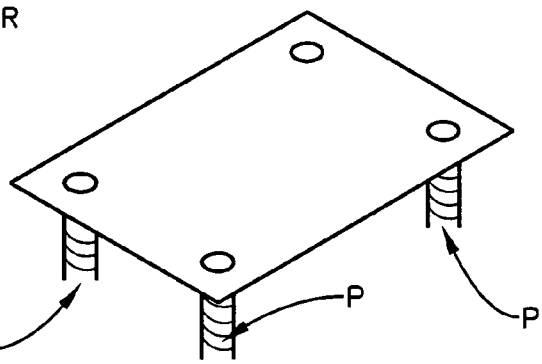
FIG. 3d demonstrates stage/sample function indicating tilt producing means.
Figure 3E:
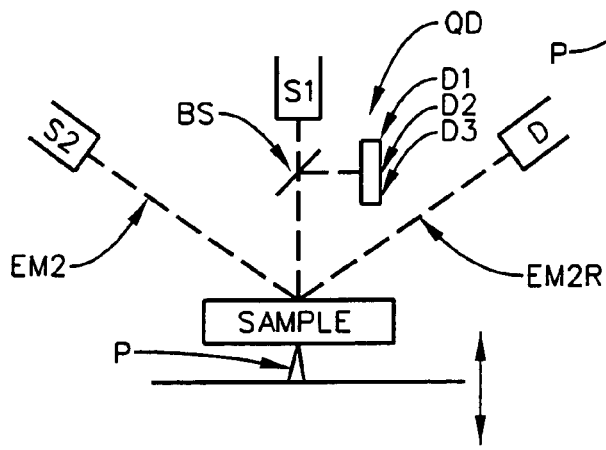
FIG. 3e shows the a system similar to that in FIG. 3c wherein the Quad Detector is positioned to receive an electromagnetic beam via a Beam Splitter (BS).

FIG. 3e shows the a system similar to that in FIG. 3c wherein the Multi-element (eg. Quad), Detector is positioned to receive an electromagnetic beam via a Beam Splitter (BS). Note that said multi-element, (eg. Quad) Detector (QD) need not have a centrally located hole therethrough in this configuration and therefore the detector elements (D1) (D2) (D3) and (D4) (which is located behind detector element (D2)), can be positioned more closely with respect to one another.

FIG. 3d demonstrates stage/sample tilt means can be corner mounted screws (P) or the like. It is to be understood that manual or automated motorized operation can be practiced.

It is noted that the Quad-detector (QD) in the Drawings can be referred to as an Alignment Detector to distinguish it from the Data Detector. Further, it is noted that said Alignment Detector need not have Four Detector Elements. Quad Detectors are a preferred embodiment, but any generally a Multi-element Detector having any functional number of Detector Elements can be applied.

It is noted that the first and beams of electromagnetic radiation from the first and second sources of electromagnetic radiation can be directed to both impinge on the sample surface at substantially the same spot, or at different locations thereupon.

Figure 4:
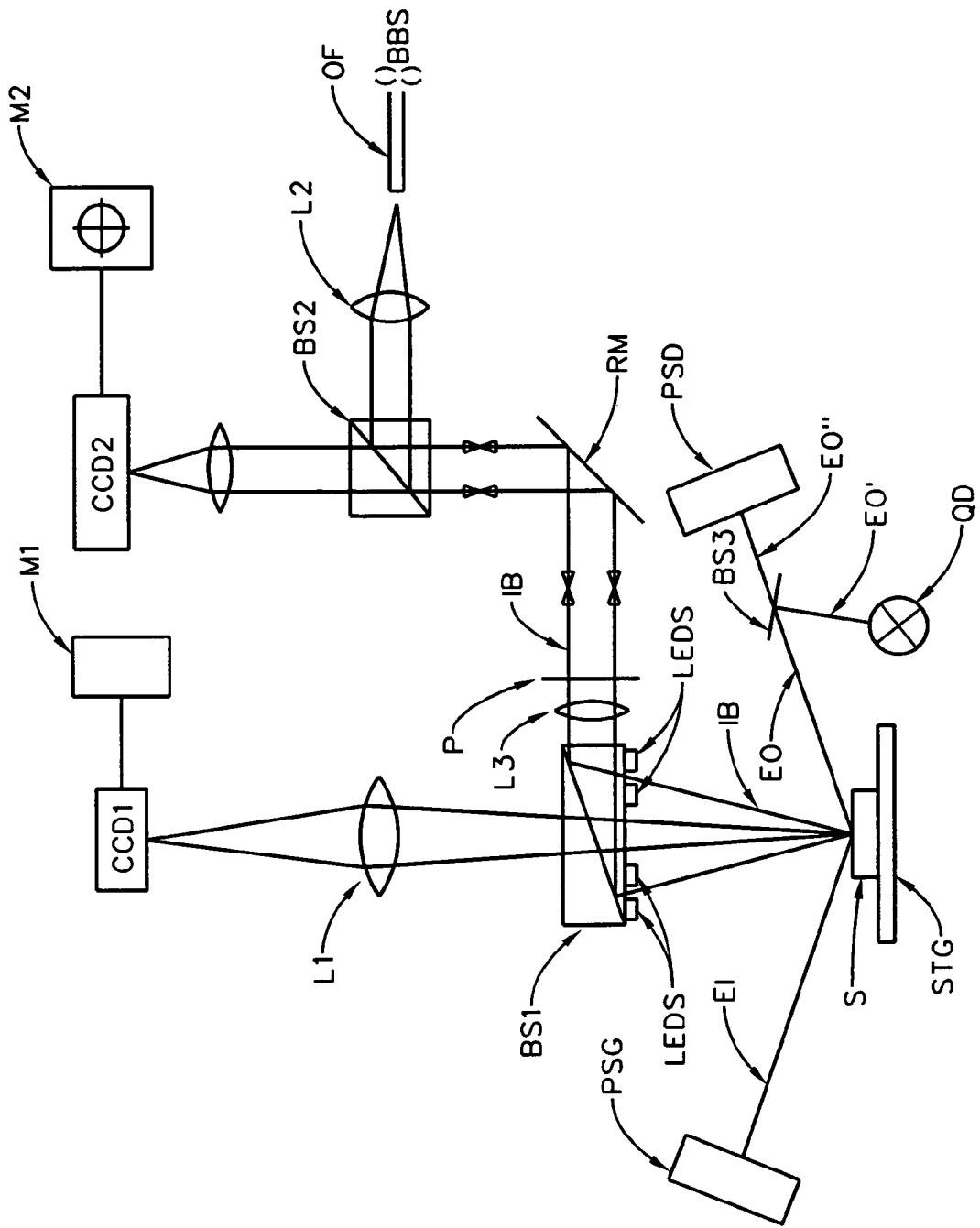
FIG. 4 shows another system for controlling the angle of incidence at which a beam of electromagnetic radiation obliquely impinges on a monitored location of a surface of a sample.

FIG. 4 shows another system for controlling the angle of incidence at which a beam of electromagnetic radiation (EI) obliquely impinges on a monitored location of a surface of a sample (S) which is present on a sample supporting stage (STG) which can be translated in "X", "Y" and "Z" directions as well as rotated about "X", "Y" and optionally "Z" axes. Said system and method of its use are subject in Co-Pending Application, and are included herein for insight. Vertically, as viewed in side elevation, above said stage (STG) there is a first beam splitter means (BS1), a Zoom lens (L1) and a first camera means (CCD1) for providing a view of a portion of the surface of said sample (S), said first beam splitter (BS1) means optionally having positioned on a lower surface thereof light emitting means (LEDS) for providing light to the surface of said sample (S). Laterally with respect to said first beam splitter means (BS1) there is a reflection means (RM), and vertically above said reflection means (RM) there is a second beam splitter (BS2). Vertically above said second beam splitter (BS2) there is a second camera means (CCD2) and laterally with respect to said second beam splitter (BS2), there is sequentially a lens (L2) and an essentially point source of electromagnetic radiation which is shown as being an Optical Fiber (OF) which receives electromagnetic radiation from source (BBS). Said first (CCD1) and second (CCD2) camera means each have associated therewith display means (M1) and (M2) respectively. Said system further comprises an ellipsometer polarization state generator (PSG) to cause, and a polarization stage detector (PSD) to monitor, a beam (EI) of electromagnetic radiation which in use impinges on said monitored location on said surface of said sample at an oblique, angle thereto. In use said first camera means (CCD1) and its associated display means provide a view of at least a portion of the surface of a sample (S) utilizing light provided by said light emitting means (LEDS) for providing light to the surface of said sample (S) and which are positioned on said lower surface of said first beam splitter (BS1), and said essentially point source of a source of electromagnetic radiation provides electromagnetic radiation to the surface of said sample via said second beam splitter (BS2), said reflective means (R) and said first beam splitter (BS1). Said sample supporting stage (STG) is caused to be translated in any of said "X", "Y" and "Z" directions as well as rotated about said "X", "Y" and optionally "Z" axes which are necessary to cause an interrogating beam (IB) of electromagnetic radiation provided by said essentially point source, (ie. fiber optic (OF)), of a source of electromagnetic radiation to reflect from the surface of said sample (S), proceed back through said first beam splitter (BS1) means, reflect from said reflective means (R), pass through said second beam splitter means (BS2), enter said second camera means (CCD2) and cause an image on the display means (M2) associated therewith which indicates that the monitored location on the sample (S) surface is oriented so as to face substantially vertically. The purpose is to align said sample (S) surface to assure that said beam of electromagnetic radiation (EI) provided to said monitored location on the surface of said sample (S) at an oblique angle approaches said surface at a known intended angle of incidence thereto at the exact point of impingement, rather than at an angle of incidence which is modified by surface irregularities.

A problem can develop in that an interrogation beam spot can appear in the image of the first camera means (CCD1) display (M1) as part of the interrogation beam and proceed through said first beam splitter (BS1) thereinto. As a solution to this problem, said system can further provide that a polarizer means (P) be placed into the path of said interrogation beam (IB) of electromagnetic radiation provided by said essentially point source of a source of electromagnetic radiation, and in which said first beam splitter (BS1) is sensitive to polarization state. The polarizer means (P) is preferable adjustable to enable changing the direction of imposed polarization. This can be beneficial where, for instance, the sample (S) has an effect on the reflected interrogation beam (IB) polarization state, and/or where it is determined desirable to allow some of said interrogation beam to reach the first camera means (CCD1), (eg. where it is found to aid with sample surface alignment).

Note that the ellipsometer system is shown to contain a Beam Splitter (BS3) and a Quad Detector (QD). Output Beam (EO) is caused partially to enter the (PSD) as (EO") and partially enter (QD) as (EO') thereby. "X" and "Y" translation of the sample (S) which cause the (AOI) of Input Beam (EI) to reflect from said Sample (S) at various (AOI) and (POI) angles show up at the (QD). When a Sample (S) is aligned so that a normal to its surface is directed vertically in the Laboratory Frame of Reference at the location of the Ellipsometer Beam (EI) Impingement thereupon small "X" and/or "Y" translations have essentially no effect on the (QD) outputs. The ellipsometer Alignment means, (ie. (BS3) and (QD)), are then utilized in the alignment procedure.

It is noted that the system of FIGS. 3a–3d can be added to the system of FIG. 4. Alternatively, (IB) in FIG. 4 can serve as a first beam of electromagnetic radiation, as said terminology is utilized in this Disclosure and a multi-element alignment detector (QD), comprised of at least two detector elements (see FIGS. 3a, 3c and 3d), optionally in functional combination with a beam splitter (see (BS) in FIG. 3d), can be added to said FIG. 4, embodiment in the pathway of the electromagnetic beam shown which transverses Zoom lens element (L1), to bring FIG. 4 within the scope of the presently disclosed invention.

It is also noted that while first and beams of electromagnetic radiation from the first and second sources of electromagnetic radiation typically are caused to impinge on the sample surface at the same spot thereupon, it is within the scope of the disclosed invention to cause said first and second electromagnetic beams to impinge at different locations thereupon.

Further, while signals from the detector elements of a multi-element alignment detector are preferably minimized, functionally this is substantially equivalent to adjusting the orientation of a sample until said signals from each alignment detector detector element are equalized.

Note, in the foregoing, the terminology Angle-Of-Incidence refers to the angle between the locus of a beam of electromagnetic radiation and a normal to a surface of a sample, and the terminology Plane-Of-Incidence refers to the plane formed by the Laboratory Normal the normal to the surface of the sample at and the locus of a beam of electromagnetic radiation at a location thereupon being investigated.

Finally, it is noted that the system of FIG. 4 can be functionally combined with the system in FIGS. 3a–3e where the beams EI and EM2 are equivalent and where beam EMI is laterally offset therefrom. In this configuration the Quad Detector (QD) in FIGS. 3a, 3b and 3d can be used to set a generally correct oreintation of a sample/stage, and the system of FIG. 4 can be used to acurately align the sample at a specific point spot.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for aligning a sample comprising:
   a pivot mounted stage/sample which is rotatable about "X", "Y" and optionally "Z" axes;
   a means for imparting translation motion to said pivot mounted stage/sample substantially along a perpendicular to a surface thereof in a "Z" direction;
   a first source of a first beam of electromagnetic radiation in functional combination with a multi-element alignment detector comprised of at least two detector elements closely surrounding a hole therethrough; and
   a second source of a second beam of electromagnetic radiation comprising a polarization state generator; and
   a data detector comprising a polarization state detector;
   said first source of a first beam of electromagnetic radiation being oriented so as to provide a first beam of electromagnetic radiation through said hole in said multi-element alignment detector;
   said pivot mounted stage/sample being positioned to receive said first beam of electromagnetic radiation substantially along a normal to a surface of said pivot mounted stage/sample via said hole in said multi-element alignment detector;
   said second source of electromagnetic radiation being positioned to provide a second beam of electromagnetic radiation and direct it to the surface of said sample at an oblique angle thereto, such that said second beam of electromagnetic radiation reflects from said surface of said pivot mounted stage/sample;
   said first and second electromagnetic beams being oriented with respect to one another at a known angle;
   said pivot mounted stage/sample being mounted to said means for imparting translation motion such that said pivot mounted stage/sample can be caused to move substantially along a perpendicular to the surface thereof in the "Z" direction, such that the reflected second beam of electromagnetic radiation enters said data detector.

2. A method of aligning a sample comprising the steps of:
   a) providing a pivot mounted stage/sample which is rotatable about "X", "Y" and optionally "Z" axes; and a means for imparting translation motion to said pivot mounted stage/sample substantially along a perpendicular to a surface thereof in the "Z" direction;

a first source of a first beam of electromagnetic radiation in functional combination with a multi-element alignment Detector comprised of at least two detector elements closely surrounding a hole therethrough; and a second source of a second beam of electromagnetic radiation comprising a polarization state generator; and a data detector comprising a polarization state detector;

said first source of a first beam of electromagnetic radiation being oriented so as to provide a first beam of electromagnetic radiation through a hole in said multi-element alignment detector;

said pivot mounted stage/sample being positioned to receive said first beam of electromagnetic radiation substantially along a normal to a surface of said pivot mounted stage/sample via said hole in said multi-element alignment detector;

said second source of a second beam of electromagnetic radiation being oriented such that a beam of electromagnetic is provided thereby at an oblique angle to the surface of said sample;

said first and second electromagnetic beams being oriented with respect to one another at a known angle;

b) causing a first beam of electromagnetic radiation from said first source of a first beam of electromagnetic to pass through said hole in the multi-element alignment detector such that said first beam of electromagnetic radiation reflects from the surface of said pivot mounted stage/sample;

c) pivoting said sample about said stage/sample pivot mounting about at least one of the "X" and "Y" axes until signals from all of the detector detector elements in the multi-element alignment detector are substantially minimized or equalized, indicating that said first beam of electromagnetic radiation approaches said surface of said sample substantially along a normal thereto;

d) causing said second source of electromagnetic radiation to provide a second beam of electromagnetic radiation and direct it to the surface of said sample at an oblique angle thereto, such that said second beam of electromagnetic radiation reflects from said surface of said pivot mounted stage/sample;

e) optionally causing said pivot mounted stage/sample to undergo translation motion substantially perpendicular to the surface of said sample in the "Z" direction via said means for imparting translation motion to said pivot mounted stage/sample in the "Z" direction;

such that the reflected second beam of electromagnetic radiation is directed to enter said data detector.

3. A method of aligning a sample as in claim 2, wherein the steps c. and e. are automated.

4. A method of aligning a sample as in claim 2, which comprises repeating the method at another location on the sample.

5. A method of aligning a sample as in claim 2, wherein the multi-element alignment detector is a quad detector comprising four detector elements.

6. A system for aligning a sample comprising:
a pivot mounted stage/sample which is rotatable about "X", "Y" and optionally "Z" axes;

a means for imparting translation motion to said pivot mounted stage/sample substantially along a perpendicular to a surface thereof in the "Z" direction;

a first source of a first beam of electromagnetic radiation in functional combination with a beam splitter and a multi-element alignment detector comprised of at least two detector elements; and a second source of a second beam of electromagnetic radiation comprising a polarization state generator; and a data detector comprising a polarization state detector;

said first source of a first beam of electromagnetic radiation being oriented so as to transmit a first beam of electromagnetic radiation through said beam splitter;

said pivot mounted stage/sample being positioned to receive said first beam of electromagnetic radiation substantially along a normal to a surface of said pivot mounted stage/sample via said beam splitter;

said multi-element alignment detector being positioned to receive electromagnetic radiation reflected from said surface of said sample which is reflected from said beam splitter;

said second source of electromagnetic radiation being positioned to provide a second beam of electromagnetic radiation and direct it to the surface of said sample at an oblique angle thereto, such that said second beam of electromagnetic radiation reflects from said surface of said pivot mounted stage/sample;

said first and second electromagnetic beams being oriented with respect to one another at a known angle;

said pivot mounted stage/sample being mounted to said means for imparting translation motion such that said pivot mounted stage/sample can be caused to move substantially along a perpendicular to the surface thereof in the "Z" direction, such that the reflected second beam of electromagnetic radiation enters said data detector.

7. A method of aligning a sample comprising the steps of:
a) providing a system for aligning a sample comprising:
a pivot mounted stage/sample which is rotatable about "X", "Y" and optionally "Z" axes;

a means for imparting translation motion to said pivot mounted stage/sample substantially along a perpendicular to a surface thereof in the "Z" direction;

a first source of a first beam of electromagnetic radiation in functional combination with a beam splitter and a multi-element alignment detector comprised of at least two detector elements; and a second source of a second beam of electromagnetic radiation comprising a polarization state generator; and a data detector comprising a polarization state detector;

said first source of a first beam of electromagnetic radiation being oriented so as to transmit a first beam of electromagnetic radiation through said beam splitter;

said pivot mounted stage/sample being positioned to receive said first beam of electromagnetic radiation substantially along a normal to a surface of said pivot mounted stage/sample via said beam splitter;

said multi-element alignment detector being positioned to receive electromagnetic radiation reflected from said surface of said sample which is reflected from said beam splitter;

said second source of electromagnetic radiation being positioned to provide a second beam of electromagnetic radiation and direct it to the surface of said sample at an oblique angle thereto, such that said second beam of electromagnetic radiation reflects from said surface of said pivot mounted stage/sample;

said first and second electromagnetic beams being oriented with respect to one another at a known angle;

said pivot mounted stage/sample being mounted to said means for imparting translation motion such that said pivot mounted stage/sample can be caused to move substantially along a perpendicular to the surface thereof, such that the reflected second beam of electromagnetic radiation enters said data detector;

b) causing a first beam of electromagnetic radiation from said first source of a first beam of electromagnetic to pass through said beam splitter such that said first beam of electromagnetic radiation reflects from the surface of said pivot mounted stage/sample, then reflects from said beam splitter and enters said multi-element alignment detector;
  c) pivoting said sample about said stage/sample pivot mounting about at least one of the "X" and "Y" axes until signals from all of the multi-element alignment detector detector elements are substantially minimized or equalized, indicating that said first beam of electromagnetic radiation approaches said surface of said sample substantially along a normal thereto;
  d) causing said second source of electromagnetic radiation to provide a second beam of electromagnetic radiation and direct it to the surface of said sample at an oblique angle thereto, such that said second beam of electromagnetic radiation reflects from said surface of said pivot mounted stage/sample;
  e) optionally causing said pivot mounted stage/sample to undergo translation motion substantially perpendicular to the surface of said sample in the "Z" direction via said means for imparting translation motion to said pivot mounted stage/sample;

such that the reflected second beam of electromagnetic radiation is directed to enter said data detector.

8. A method of aligning a sample as in claim 7, wherein the steps c. and e. are automated.

9. A method of aligning a sample as in claim 7, which comprises repeating the method at another location on the sample.

10. A method of aligning a sample as in claim 7, wherein the multi-element alignment detector is a quad detector comprising four detector elements.

11. A system as in claim 1 in which the multi-element alignment detector is a quad detector comprising four detector elements.

12. A system as in claim 6 in which the multi-element alignment detector is a quad detector comprising four detector elements.

13. A method of aligning a sample as in claim 2 in which the first and beams of electromagnetic radiation from the first and second sources of electromagnetic radiation to both impinge on the sample surface at substantially the same spot.

14. A method of aligning a sample as in claim 3 in which the first and beams of electromagnetic radiation from the first and second sources of electromagnetic radiation to both impinge on the sample surface at substantially the same spot.

15. A method of aligning a sample as in claim 7 in which the first and beams of electromagnetic radiation from the first and second sources of electromagnetic radiation both impinge on the sample surface at substantially the same spot.

16. A method of aligning a sample as in claim 2 in which the first and beams of electromagnetic radiation from the first and second sources of electromagnetic radiation impinge on the sample surface at different locations.

17. A method of aligning a sample as in claim 3 in which the first and beams of electromagnetic radiation from the first and second sources of electromagnetic radiation impinge on the sample surface at different locations.

18. A method of aligning a sample as in claim 7 in which the first and beams of electromagnetic radiation from the first and second sources of electromagnetic radiation impinge on the sample surface at different locations.

* * * * *